United States Patent
Metz-Stavenhagen

Patent Number: 5,707,371
Date of Patent: Jan. 13, 1998

[54] REPOSITIONING TOOL

[75] Inventor: Peter Metz-Stavenhagen, Bad Wildungen, Germany

[73] Assignee: Howmedica GmbH, Schoenkirchen, Germany

[21] Appl. No.: 689,550

[22] Filed: Aug. 9, 1996

Related U.S. Application Data

[63] Continuation of Ser. No. 523,850, Sep. 5, 1995, abandoned, which is a continuation of Ser. No. 358,033, Dec. 15, 1994, abandoned, which is a continuation of Ser. No. 23,493, Feb. 26, 1993, abandoned.

[30] Foreign Application Priority Data

Feb. 28, 1992 [DE] Germany .............................. 9202587 U

[51] Int. Cl.⁶ .................................................. A61B 17/56
[52] U.S. Cl. ................................ 606/61; 606/73; 606/104
[58] Field of Search ........................... 606/61, 73, 72, 606/74, 104, 86, 96, 60, 206, 207, 208; 81/340, 426.5, 418, 901

[56] References Cited

U.S. PATENT DOCUMENTS

| | | |
|---|---|---|
| 1,293,696 | 2/1919 | Bush ......................... 81/426.5 |
| 1,310,510 | 7/1919 | Speirs ....................... 81/426.5 |
| 2,567,182 | 9/1951 | Cohen ......................... 81/323 |
| 4,539,874 | 9/1985 | Jacovitz . |
| 4,790,303 | 12/1988 | Steffee . |
| 4,940,454 | 7/1990 | Siragusa .................... 606/207 |

FOREIGN PATENT DOCUMENTS

| | | | |
|---|---|---|---|
| 328883 | 8/1989 | European Pat. Off. ........ 606/61 |
| 2510022 | 1/1983 | France . | |
| 3804749 | 3/1989 | Germany . | |
| 9112466 | 1/1992 | Germany . | |
| 2214814 | 9/1989 | United Kingdom ......... 606/104 |

*Primary Examiner*—Guy V. Tucker
*Attorney, Agent, or Firm*—Peter C. Richardson; Lawrence C. Akers; Elizabeth O. Slade

[57] ABSTRACT

A repositioning tool for handling pedicle screws which have annular heads with parallel clamping faces is provided. The tool has a tongue-shaped portion connected to a handle, which tongue-shaped portion is brought into engagement with the head of a pedicle screw in the axial direction thereof. The tool can apply a tilting moment perpendicular to the length axis of the pedicle screw and can apply a torque. The tool comprises pliers with jaws (22, 24) including inwardly extending projections (28, 30) to engage opposite indentations (70, 72) provided along the periphery of the annular head (64) of the pedicle screw (60).

13 Claims, 1 Drawing Sheet

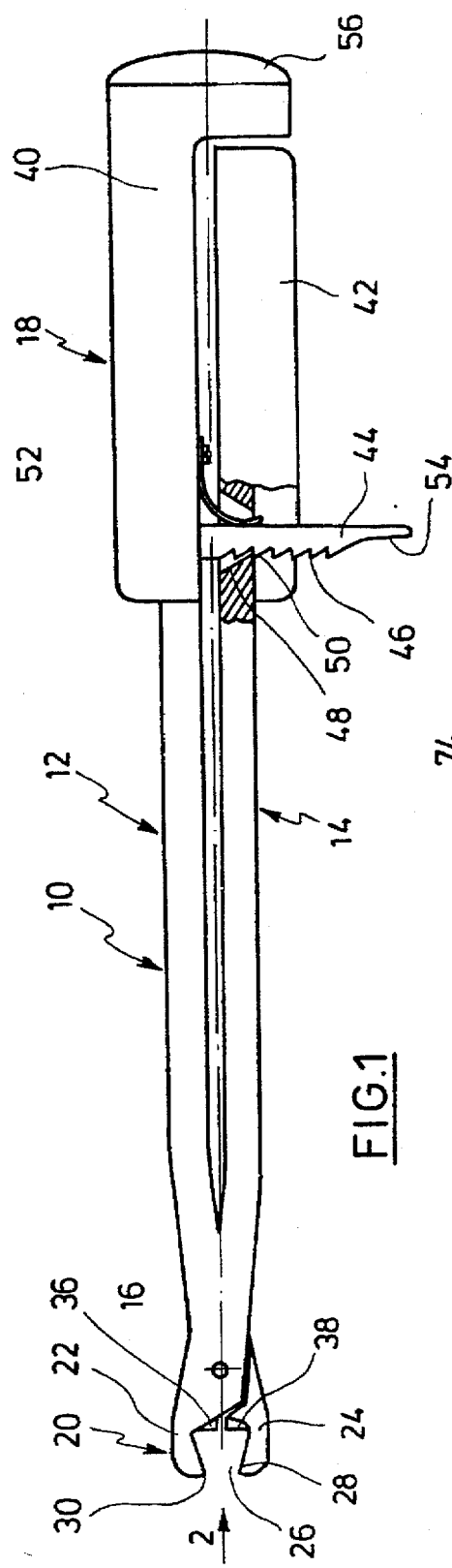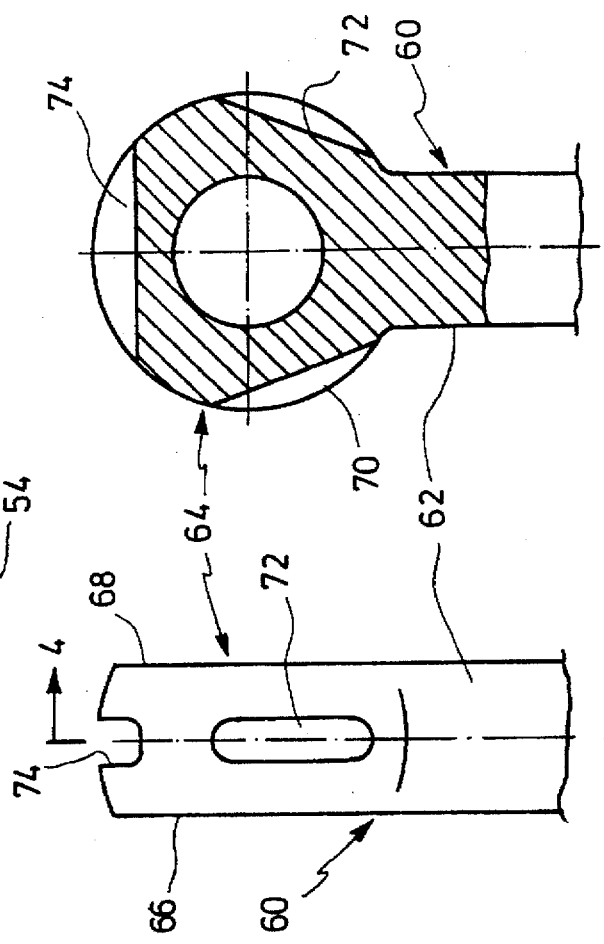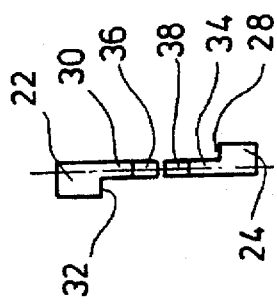

REPOSITIONING TOOL

This is a continuation of application Ser. No. 08/523,850, filed on Sep. 5, 1995, now abandoned, which is a continuation of U.S. Ser. No. 08/358,033, filed on Dec. 15, 1994, now abandoned, which is a continuation of U.S. Ser. No. 08/023,493, filed on Feb. 26, 1993, now abandoned.

The present invention relates to a repositioning tool for handling pedicle screws.

Pedicle screws which are dorsally screwed into the pedicle of the human spine form known components of means for supporting the human spine. EP 0 328 883 discloses a supporting means according to which the annular head of the pedicle screws include opposite clamping faces to mount a pair of pedicle screws at a distance from each other by using a tensioning means which can be shaped like a so-called turnbuckle to apply a pulling force or a pressure to the pedicle screws. The pedicle screws mounted in the vertebra are used to exercise a repositioning in adjusting the screws with respect to each other by a suitable handle means until the vertebra to be repositioned has obtained the proper position. For repositioning, a tool is required which effectively grips a pedicle screw and which allows one to apply a suitable torque. It is known to embrace the head of a pedicle screw in its longitudinal axis and to engage the portion of the screw shaft adjacent the head by a suitable handling means to apply a torque normal to the axis of the screw shaft. The known device is relatively large so that the view of the surgeon to the projecting end of the pedicle screw is obstructed. Furthermore, it is difficult to operate the clamping screw extending through the head of the pedicle screw when the device is in engagement with the pedicle screw.

Conceivably a repositioning may be performed by the tensioning means already mounted. However, the tensioning means is regularly mounted in close proximity to the spine so that handling is difficult. Furthermore, the adjusting range of the tensioning means is rather limited.

Therefore it is an object of the present invention to provide a tool for handling pedicle screws which is easily operated, is suited to apply high forces to the pedicle screws and lends itself to a simple application of tensioning means or the like.

The objects referred to are solved by the device of the invention.

SUMMARY OF THE INVENTION

The tool according to the invention is formed as a pliers, wherein the jaws include projections facing inwardly. The annular head of a pedicle screw is provided with peripherally opposite indentations which are engaged by the projections. Between the projections and the indentations a positive engagement is preferred to apply a rotation as well as a cross force to the shaft of the pedicle screw.

According to an embodiment of the invention the width of the jaws is selected to be smaller than the thickness of the pedicle screw head and the width of the projections is selected to be smaller than the width of the jaws, wherein the jaws are located off-set (see FIG. 2) with respect to each other. Thus, the head of a pedicle screw is effectively gripped, even when the pedicle screw is clamped to a tensioning means for example. Depending on which side an attachment is provided, two different jaws are required, i.e. one for the left and one for the right usage.

In a still further embodiment of the invention the outer faces of the projections facing each other converge towards the opening of the jaws to engage the indentations substantially beyond the center of the screw head opening. Accordingly, a pulling force may be effectively applied to the pedicle screw.

In a further preferred embodiment, the projections are triangular and the indentations include a plane bottom, wherein the bottoms of both the opposite indentations converge towards the screw shaft. Such indentations weaken the screw head very little, but afford an effective form-fit for the application of relatively high forces from the pliers to the pedicle screw.

In order to completely utilize the strength of the jaws having a predetermined width, the invention provides for an embodiment according to which the projections each are flush with an outer face of the respective jaw. To further improve the application of forces to the pedicle screw, an embodiment of the invention provides jaws including an inner abutment portion for engaging the peripheral portion of the screw head opposite the screw shaft. Preferably, there is provided a third indentation which is engaged by the abutment portions of the jaws. A positive form-fit of the cooperating parts is preferred.

Conceivably, the handles of the pliers can be manually pressed together when a screw head is engaged. According to the invention, however, it is preferred to provide a locking arm to one gripping leg of the pliers, preferably within the handle area, the locking arm extending across or through the other gripping leg and cooperating with locking teeth or the like provided at the other gripping leg. Accordingly, the jaws are arrested in the gripping position and the surgeon exclusively attends to operating the pedicle screw.

In a further embodiment of the invention the locking arm is preferably biased by a spring towards the locking teeth. The locking arm may be formed as a resilient member or can be pivotally mounted in the gripping leg.

DESCRIPTION OF THE PREFERRED EMBODIMENTS

A preferred embodiment of the invention is described in detail by referring to the accompanying drawings which show:

FIG. 1 a side view of the tool according to the invention, partly in section,

FIG. 2 the front view of the tool of FIG. 1 in the direction of arrow 2,

FIG. 3 a side view of the upper portion of a pedicle screw,

FIG. 4 a section through the pedicle screw of FIG. 3 along line 4—4.

FIG. 1 shows a pliers 10 comprising a pair of levers 12 and 14 which are pivotally linked together at 16. the levers define a handle portion 18 at one end and a tongue-shaped jaw portion 20 at the other end.

The jaw portion 20 is formed by a pair of jaws 22, 24 defining a mouth 26 therebetween. As shown in FIGS. 1 and 2, each leg 22, 24 includes a triangular projection 28, 30, wherein the straight faces of the projections 28, 30 converge towards the mouth opening. As FIG. 2 shows, the projections 28, 30 have a smaller width w' than the jaws 22, 24 (the width of which is w) and they are arranged in a common plane. At one side the projections are flush with the outer leg 22 or, respectively 24, whereas a shoulder 32 or 34 is formed at the other side. The inner side of the mouth 26 is integrally provided with abutment portions 36, 38 which engaging faces are plane and are aligned with respect to each other.

In the handle portion, handles 40, 42 are attached to the lever arms. A locking arm 44 is connected to the lever 12 or, respectively, the handle 40, which locking arm projects approximately perpendicular and which locking arm is provided with saw teeth 46. The locking arm 44 extends through an opening 48 in the lever 14 defining a locking tooth 50 at its outer edge. A curved leaf spring 52 attached to the handle 40 engages the locking arm 44 opposite the saw teeth 46. An end portion 54 of the locking arm 44 may be actuated to release the teeth 46 from the locking tooth 50 in order to open the pliers 10. The rear end of the handle 40 is provided with a projecting portion 56 to extend beyond the rear end of the shorter handle 42 to improve the handling of the pliers.

FIGS. 3 and 4 show a pedicle screw 60 including a threaded shaft 62 and an annular head 64. Pedicle screws with a ring-shaped head are generally known. Conventionally, a clamping face is provided on opposite faces 66, 68 which clamping face may be toothed to be engaged by a tensioning means or the like. The periphery of the head 64 is provided with a pair of opposite indentations 70, 72. They are located substantially below the diameter through the head 64 extending perpendicular through the axis of the shaft 62. The straight bottoms of the indentations 70, 72 converge towards the shaft 62. For example, they form an angle between 20° to 30°. The dimensions of the indentations 70, 72 are such that the projections 28, 30 are substantially positively engaged. A third indentation 74 at the periphery of the head 64 is provided with a straight bottom as well which extends substantially perpendicular to the shaft axis. The indentation 74 is provided such that the abutment portions 36, 38 substantially positively engage. All three indentations 70, 72, 74 are lengthwise centered with respect to the width of the head 64 and the width of the indentations is noticeably smaller than the width of the head. The width of the jaws 22, 24 is selected to never extend beyond the front faces 66, 68 of the head 64 when the projections 28, 30 and the abutment portions 36, 38 are located in the indentations 70, 72 and 74. In this case the head 64 is positively clamped by the pliers to apply forces to the shaft 62 in all directions.

I claim:

1. A method for repositioning and handling a pedicle screw having an annular head including parallel clamping faces on opposite sides of said annular head to be connected to at least a tensioning means, said method comprising:

bringing a tongue-shaped pliers portion connected to a pliers handle into engagement with the head of said pedicle screw in the axial direction thereof to apply a tilting moment perpendicular to the length axis of said pedicle screw and to apply a torque, wherein said pliers (10) portion comprises jaws (22, 24) meeting at a pivot pin and having a jaw mouth (26) with a jaw mouth opening and including inwardly extending projections (28, 30)

so that said inwardly extending projections (28, 30) engage opposite indentions (70, 72) having plane bottoms and provided along the periphery of the annular head (64) of said pedicle screw (60).

2. The method of claim 1, wherein said jaws (22, 24) have a jaw width w, said head of said pedicle screw has a width W and the jaw width w is smaller than the width W of the head (64) of the pedicle screw (60) and wherein the width w' of said projections (28, 30) is smaller than the width w of the jaws (22, 24) and wherein the jaws (22, 24) are offset with respect to each other.

3. The method of claim 2, wherein projections (28, 30) have outer faces, wherein said outer faces of said projections (28, 30) facing each other converge towards said jaw mouth opening to engage indentations (70, 72) substantially in an area below the diameter of said annular head (64) of said pedicle screw (60) extending perpendicular to said length axis of said pedicle screw.

4. The method of claim 3, wherein said pedicle screw has a screw shaft (62), wherein the projections (28, 30) are triangular and the indentations (70, 72) each include a plane bottom, and wherein the bottoms of the opposite indentations (70, 72) converge towards said screw shaft (62).

5. The method of claim 4, wherein the bottoms include an angle of 20° to 30°.

6. The method of claim 5, wherein a projection (28, 30) has a side which is flush with an outer face of a jaw (22, 28).

7. The method of claim 6, wherein the jaws (22, 24) include an inner abutment portion (36, 38) each for engaging a peripheral portion of the screw head (64) opposite the screw shaft (62).

8. The method of claim 7 wherein said abutment portions (36, 38) are formed by lugs extending toward said jaw mouth opening, which lugs commonly engage a third indentation (74) provided along said peripheral portion of said screw head (64).

9. The method of claim 8, wherein said abutment portions (36, 38) have plane faces to cooperate with a plane bottom of a third indentation (74) of said screw head (64).

10. The method of claim 9, wherein said pliers handle has a first handle portion and a second handle portion in a gripping area (18) and wherein said first handle portion is provided with a locking arm (44) arranged in said gripping area (18), and said locking arm cooperating with a locking tooth (50) is attached to said second handle portion.

11. The method of claim 10, wherein said locking arm (44) is pivotally mounted, said locking arm being biased by a spring (52) towards said locking tooth (50) at least when pivotally mounted.

12. A method for handling a pedicle screw which has an annular head including parallel clamping faces on opposite sides of said head, said method comprising:

(1) grasping said pedicle screw with a tool comprising pliers having:
 (a) a handle portion and
 (b) a jaw portion having a tongue-shape and connected to said handle portion, and (2) bringing said jaw portion into engagement with the head of said pedicle screw so as to apply a tilting moment perpendicular to the length axis of said pedicle screw and to apply a torque,
 wherein said jaw portion comprises a first jaw and a second jaw meeting at a pivot pin and having inwardly extending projections for engagement of corresponding indentations provided along the periphery of said annular head of said pedicle screw.

13. A method for handling pedicle screws including an annular head having head indentations on opposite sides of the periphery of said head, a threaded shank, and a longitudinal axis, said method comprising:

(1) bringing a pliers having a pair of jaws with inwardly extending projections facing each other and connected to crossing handle portions into engagement with said head indentations such that said pliers is coaxial with said longitudinal axis and (2) exerting a tilting force on said pedicle screw transverse to said longitudinal axis and exerting a torque on said pedicle screw.

* * * * *